(12) United States Patent
Kim et al.

(10) Patent No.: US 7,347,967 B2
(45) Date of Patent: Mar. 25, 2008

(54) PLASTIC SYSTEM AND METHOD OF POROUS BIOIMPLANT HAVING A UNIFIED CONNECTOR

(75) Inventors: Kiju Kim, Pohang-si (KR); Wonhee Lee, Seoul (JP); Jongkyun Jung, Pohang-si (KR)

(73) Assignee: Isan Biotech Co., Seoul (KR)

( * ) Notice: Subject to any disclaimer, the term of this patent is extended or adjusted under 35 U.S.C. 154(b) by 339 days.

(21) Appl. No.: 10/468,835

(22) PCT Filed: Nov. 3, 2001

(86) PCT No.: PCT/KR01/01864

§ 371 (c)(1),
(2), (4) Date: Sep. 2, 2003

(87) PCT Pub. No.: WO02/069835

PCT Pub. Date: Sep. 12, 2002

(65) Prior Publication Data

US 2004/0076538 A1    Apr. 22, 2004

(30) Foreign Application Priority Data

Mar. 2, 2001 (KR) ............... 2001-10792
Nov. 3, 2001 (KR) ............... 2001-08347

(51) Int. Cl.
*B22F 3/11* (2006.01)

(52) U.S. Cl. ............... 419/2; 419/10; 419/52

(58) Field of Classification Search .......... 419/2, 419/10, 52; 266/200
See application file for complete search history.

(56) References Cited

U.S. PATENT DOCUMENTS

| | | | | |
|---|---|---|---|---|
| 4,929,415 A | * | 5/1990 | Okazaki ............ | 419/52 |
| 5,027,998 A | * | 7/1991 | Bugle ............ | 228/44.5 |
| 6,066,274 A | * | 5/2000 | Antonson et al. ...... | 264/16 |

* cited by examiner

*Primary Examiner*—Scott Kastler
(74) *Attorney, Agent, or Firm*—Lowe Hauptman Ham & Berner LLP (57) ABSTRACT

The present invention relates to a system and a method of manufacturing a porous bio-implant having a connecting member integrally formed therewith, and more particularly, to a system and a method of manufacturing a porous bio-implant in which a connecting member is integrally formed by sintering a metal powder by a high voltage instant discharge in the state that the connecting member is inserted in a pyrex tube and then the metal powder is put in the pyrex tube. A system of manufacturing a porous bio-implant having a connecting member formed integrally therewith includes a power supply supplying a low voltage; a voltage booster for boosting the low voltage supplied from the power supply to a high voltage; a condenser charging the high voltage boosted by the voltage booster through a switch; a vacuum switch for instantaneously discharging the high voltage charged in the condenser; and a bio-implant manufacturing apparatus for manufacturing a bio-implant by the high voltage discharged instantaneously from the vacuum switch.

8 Claims, 8 Drawing Sheets

PLASTIC SYSTEM AND METHOD OF POROUS BIOIMPLANT HAVING A UNIFIED CONNECTOR

This is a nationalization of PCT/KR01/01864 filed Nov. 3, 2001 and published in English.

TECHNICAL FIELD

The present invention relates to a system and a method of manufacturing a porous bio-implant having a connecting member integrally formed therewith, and more particularly, to a system and a method of manufacturing a porous bio-implant in which a connecting member is integrally formed by sintering a metal powder by a high voltage instant discharge in the state that the connecting member is inserted into a pyrex tube and then the metal powder is put in the pyrex tube.

BACKGROUND ART

A conventional non-porous implant of a screw type and a conventional porous implant manufactured by a high temperature sintering are described with reference to FIGS. 1 and 2.

Figure 1:
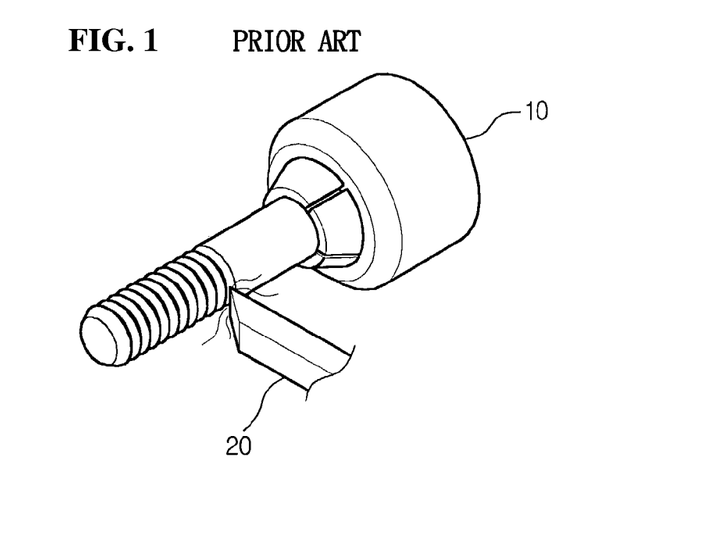
FIG. 1 is a perspective view illustrating a screw-type implant manufactured by a mechanical processing according to a conventional art.

FIG. 1 is a perspective view illustrating a porous screw-type implant manufactured by a mechanical processing according to a conventional art. FIG. 2 is a front view illustrating an implant manufactured by a high temperature sintering according to a conventional art.

A screw-type implant 10 is manufactured by a mechanical processing using a milling machine 20. Thus, a processing is very difficult, and a lengthy processing time is required. Also, due to a formation of an oxide film by a secondary processing, a manufacturing cost is high. In addition, a bonding power is poor due to a small contacting area to a bone or a fibrous tissue when implanted into body tissue, and therefore the implant 10 can be easily removed from the body tissue. In the case that a large-sized implant is implanted into body tissue so as to overcome this problem, a treatment time period becomes lengthy, and the implant can locally be implanted into only body tissue having a relatively high bone density and having a large size.

In effort to overcome these problems, a method of manufacturing a porous implant by sintering metal powders at a high temperature has been introduced.

Figure 2:
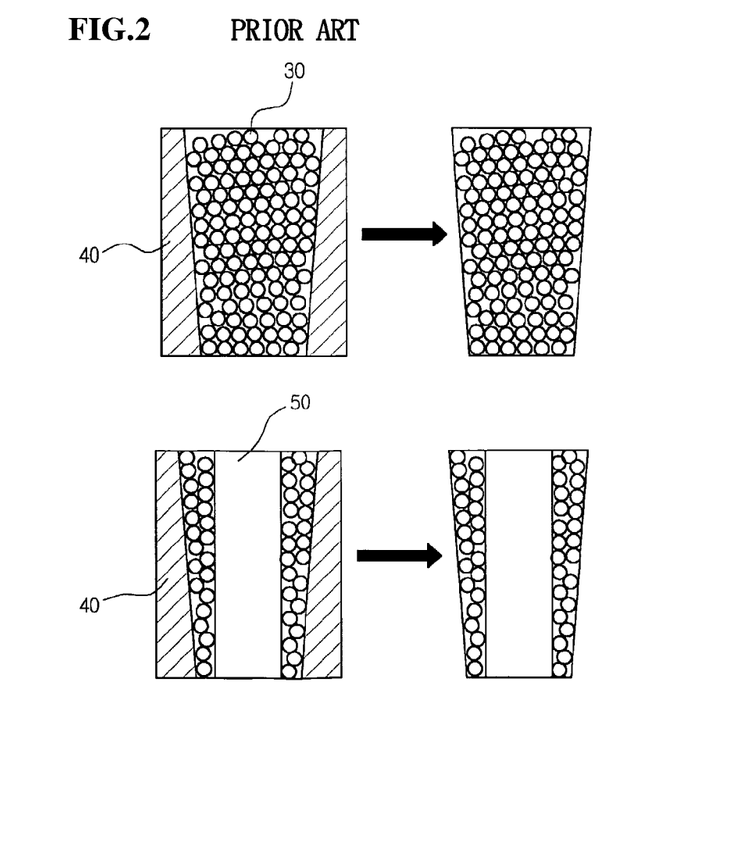
FIG. 2 is a front view a porous implant manufactured by a high temperature sintering according to a conventional art.

As shown in FIG. 2, metal powders 30 are put in a mold 40 and sintered at a high temperature during a long time period. Or, as shown in FIG. 2B, after putting the metal powers in the mold 40, a bar 50 is inserted to pass through a central portion of the metal powders 30, and the metal powders 30 are sintered at a high temperature during a long time period.

However, the method of FIG. 2 has a problem in that a metal inherent nature variation, a low durability, a surface variation, a lengthy sintering, and a high production cost.

Accordingly, there is a need for a technique of manufacturing a new implant in which a production cost is low, a contacting area between the implant and the bone is improved, a bonding power between the implant and the bone, a durability is high, a life span is lengthy, a treatment period is short, and a compression strength can be adjusted by adjusting a size of the implant.

DISCLOSURE OF INVENTION

To overcome the problems described above, preferred embodiments of the present invention provide a system and a method of manufacturing a porous bio-implant having a connecting member formed integrally therewith in which does not require subsequent processes because a metal power in a pyrex tube is sintered by a high temperature instant discharge and so attached to the connecting member.

It is another object of the present invention to provide a system and a method of manufacturing a porous bio-implant having a connecting member formed integrally therewith which can adjust a compression strength according to a location of respective teeth by adjusting a size of the connecting member.

The system of manufacturing a porous bio-implant having a connecting member formed integrally therewith includes a power supply for supplying a low voltage; a voltage booster for boosting the low voltage supplied from the power supply to a high voltage; a condenser charging the high voltage boosted by the voltage booster through a switch; a vacuum switch for instantaneously discharging the high voltage charged in the condenser; and a bio-implant manufacturing apparatus for manufacturing a bio-implant by the high voltage discharged instantaneously from the vacuum switch.

The bio-implant manufacturing apparatus includes a hollow pyrex tube; the connecting member inserted into the pyrex tube; a metal powder inserted in an inner space of the pyrex tube under the connecting member; an upper electrode inserted into an upper opening of the pyrex tube and rested on an upper surface of the connecting member; and a lower electrode inserted into a lower opening of the pyrex tube to pressurize the metal powder.

The connecting member includes a connecting member main; a header portion integrally formed on an upper central portion of the connecting member main, and a screw hole formed in a predetermined depth under the header portion.

The lower electrode has a concave groove formed in a predetermiend depth. The bio-implant manufactured by the bio-implant manufacturing apparatus is integrally formed with the connecting member by sintering the metal powder by combination of a pinch pressure and a heat energy, and has a porous layer on an outer surface thereof.

A surface roughness of the bio-implant manufactured by the bio-implant manufacturing apparatus is determined by adjusting a size of the metal powder. A compression strength of the bio-implant manufactured by the bio-implant manufacturing apparatus is determined by adjusting a size of the connecting member.

A method of manufacturing a porous bio-implant having a connecting member formed integrally therewith includes the steps of: inserting the connecting member into a pyrex tube through an upper opening of the pyrex tube; inserting a metal powder into the pyrex tube through a lower opening of the pyrex tube; inserting an upper electrode through the upper opening of the pyrex tube and resting the upper electrode on the upper surface of the connecting member, and inserting a lower electrode through the lower opening of the pyrex tube; supplying a low voltage from a power supply connected to the upper and lower electrodes; boosting the low voltage to a high voltage by a voltage booster; charging the high voltage boosted by the voltage booster in the condenser through a switch; discharging the high voltage charged in the condenser instantaneously through the vacuum switch; and sintering the metal powder in the pyrex tube, thereby forming a porous bio-implant integrally with the connecting member.

BRIEF DESCRIPTION OF DRAWINGS

For a more complete under supporting of the present invention and the advantages thereof, reference is now made to the following descriptions taken in conjunction with the accompanying drawings, in which like reference numerals denote like parts, and in which.

BEST MODE FOR CARRYING OUT THE INVENTION

Reference will now be made in detail to preferred embodiments of the present invention, example of which is illustrated in the accompanying drawings. Like reference numerals denote like parts.

Figure 3:
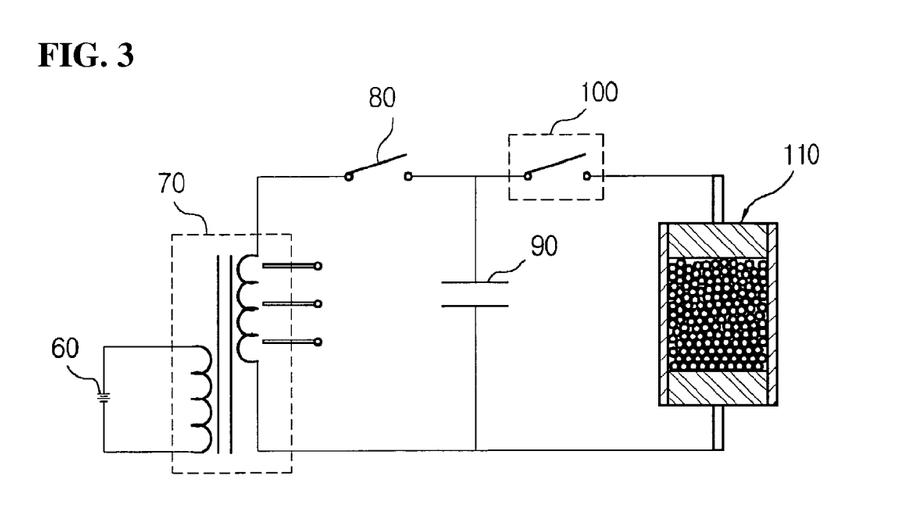
FIG. 3 is a circuit diagram a porous bio-implant manufacturing system according to one embodiment of the present invention.
Figure 4:
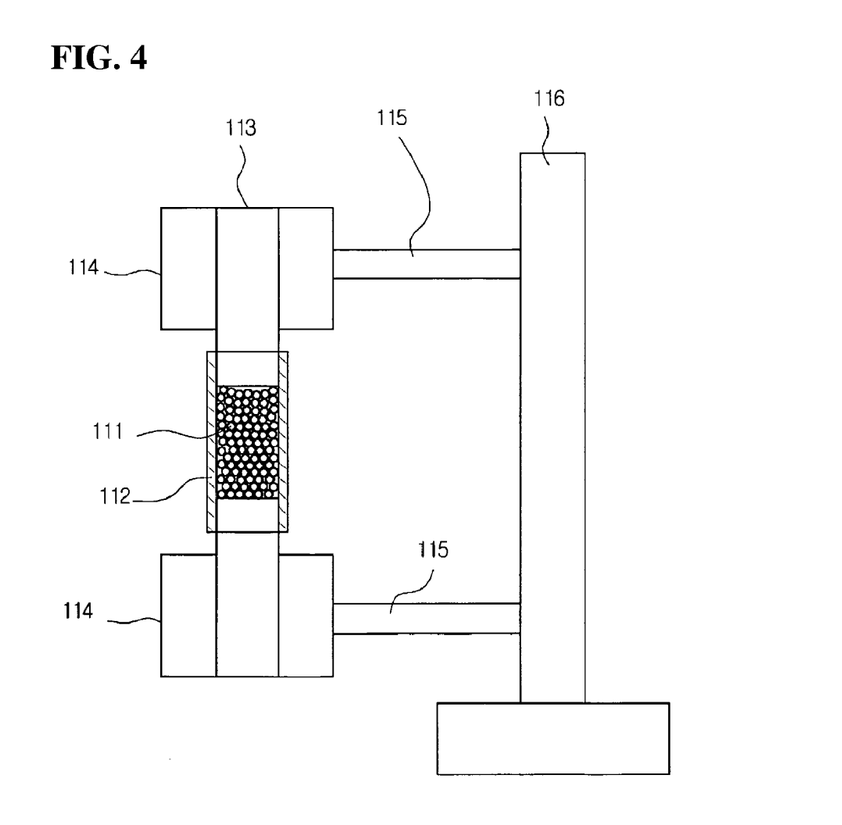
FIG. 4 shows the porous bio-implant manufacturing apparatus according to the present invention
Figure 5:
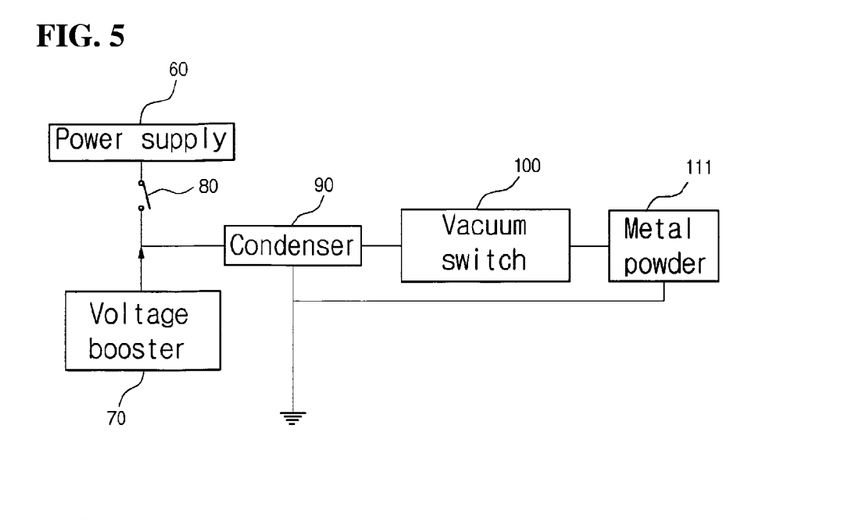
FIG. 5 is a block diagram illustrating the porous bio-implant manufacturing system according to one embodiment of the present invention.
Figure 6:
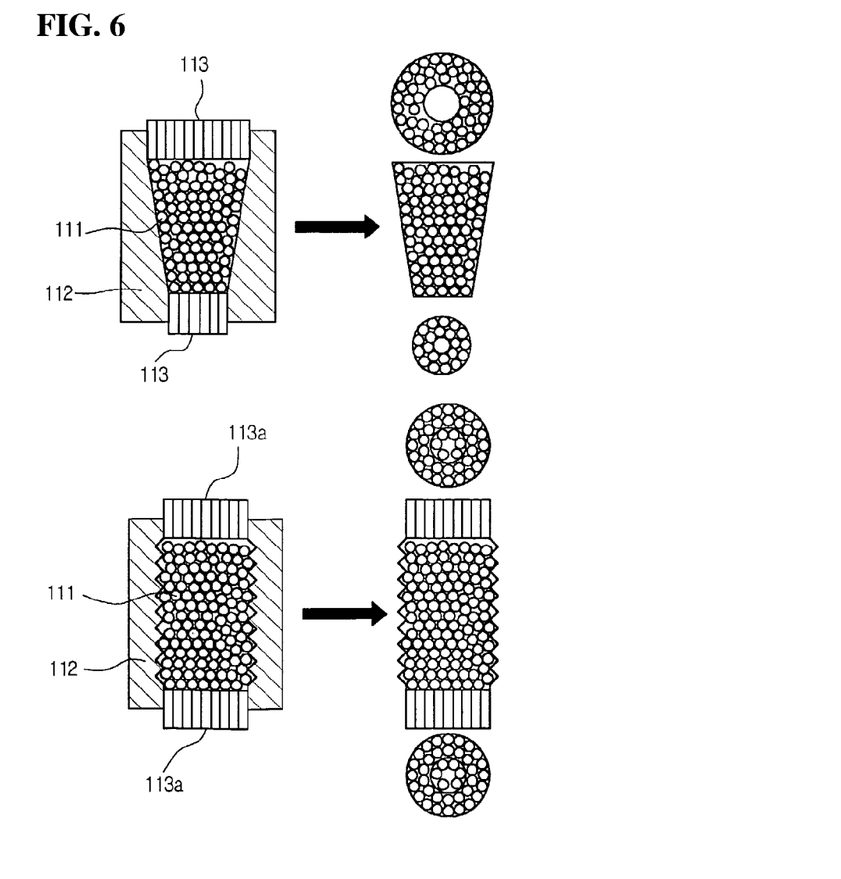
FIG. 6 is a cross-sectional view illustrating various pyrex tubes according to one embodiment of the present invention.
Figure 7:
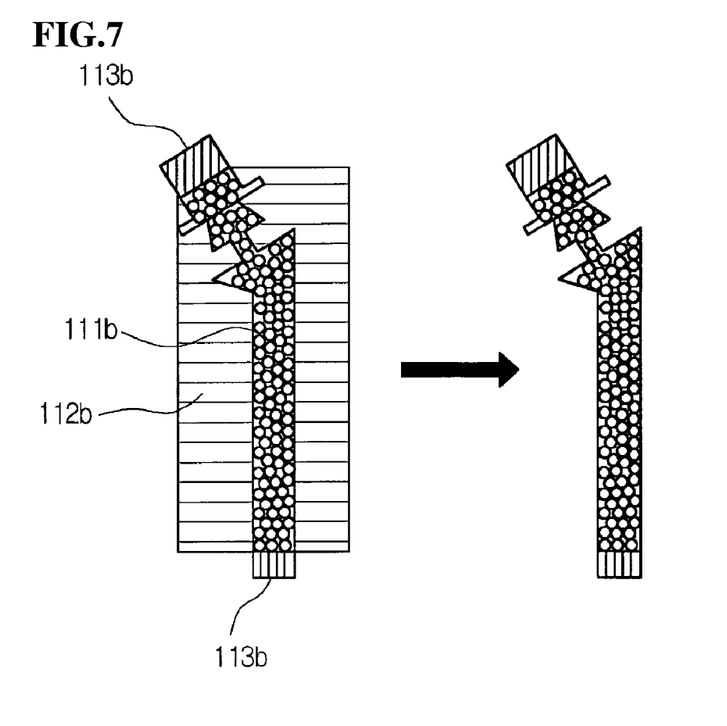
FIG. 7 is a front view illustrating a porous bio-implant manufactured according to one embodiment of the present invention.
Figure 8:
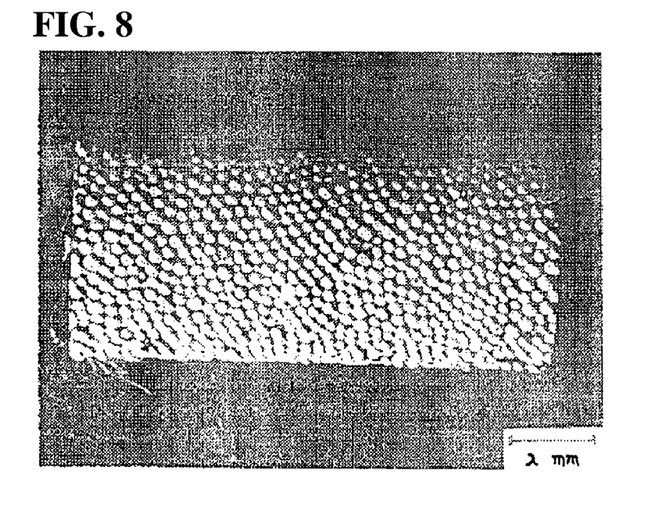
FIG. 8 is a cross-sectional view illustrating the porous bio-implant manufactured according to one embodiment of the present invention.
Figure 9:
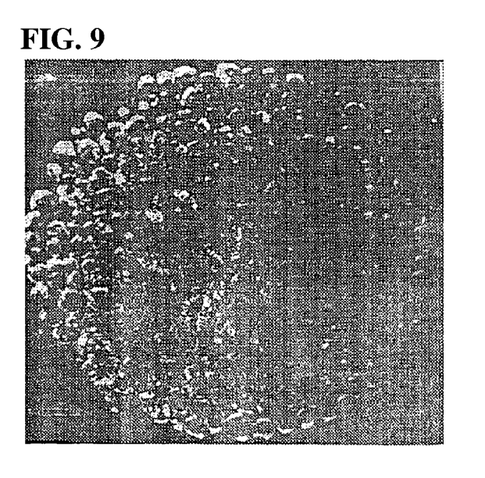
FIG. 9 is a front view illustrating a porous layer of the porous bio-implant manufactured to one embodiment of the present invention.
Figure 10:
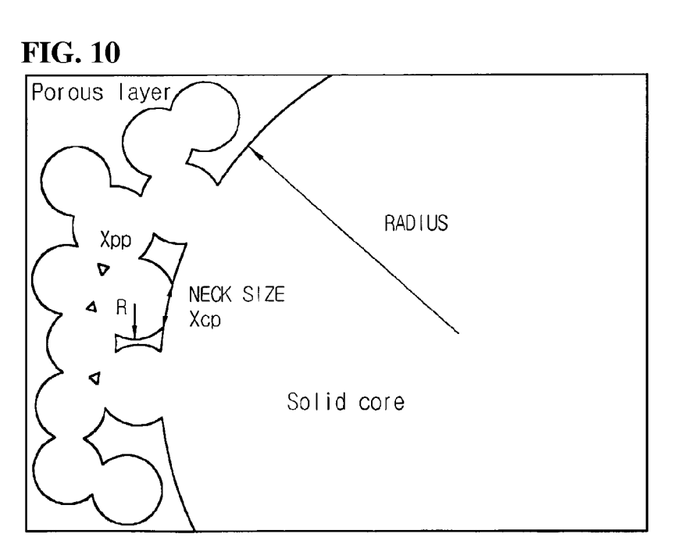
FIG. 10 is a front view illustrating pores of the porous layer of the porous bio-implant manufactured to one embodiment of the present invention.

FIG. 3 is a circuit diagram a porous bio-implant manufacturing system according to one embodiment of the present invention. FIG. 4 shows the porous bio-implant manufacturing apparatus according to the present invention. FIG. 5 is a block diagram illustrating the porous bio-implant manufacturing system according to one embodiment of the present invention. FIG. 6 is a cross-sectional view illustrating various pyrex tubes according to one embodiment of the present invention. FIG. 7 is a front view illustrating a porous bio-implant manufactured according to one embodiment of the present invention. FIG. 8 is a cross-sectional view illustrating the porous bio-implant manufactured according to one embodiment of the present invention. FIG. 9 is a front view illustrating a porous layer of the porous bio-implant manufactured to one embodiment of the present invention. FIG. 10 is a front view illustrating pores of the porous layer of the porous bio-implant manufactured to one embodiment of the present invention.

The porous bio-implant manufacturing system includes a power supply 60, a voltage booster 70, a first switch 80, a condenser 90, a vacuum switch 100, and a porous bio-implant manufacturing apparatus 110.

The porous bio-implant manufacturing apparatus 110 includes a pyrex tube 112, 112a or 112b to which a metal powder 111, 111a or 111b, upper and lower electrodes 113, 113a or 113b which is inserted into and attached to the pyrex tube 112, 112a or 112b, upper and lower electrode holders 114, upper and lower suspension members 115, and a main support 116.

The pyrex tube 112, 112a or 112b are hollow, and the metal powder 111, 111a or 111b is put on the middle of the pyrex tube 112, 112a or 112b. The pyrex tube 112, 112a or 112b is preferably made of quartz, and can have various shapes.

The upper and lower electrodes 113, 113a or 113b are inserted into and attached to both upper and lower openings of the pyrex tube 112, 112a or 112b. The upper and lower electrode holders 114 firmly hold the upper and lower electrodes 113, 113a or 113b. The upper and lower electrodes 113, 113a or 113b are preferably made of copper or brass.

The upper and lower suspension members 115 connect the upper and lower electrode holders 114 to the main support 116, respectively.

Operation of the porous bio-implant manufacturing system is described below.

A low voltage of 100 volts or 200 volts is supplied from the power supply 60. The voltage booster 70 boosts the low voltage to a high voltage of 1000 volts to 5000 volts and preferably to a high voltage of 2500 volts. The high voltage passes through the first switch 80 and charges the condenser 90. The high voltage charged in the condenser 90 are discharged instantaneously through the vacuum switch 100 to sinter the metal powder 111, 111a or 111b in the pyrex tube 112, 112a or 112b, thereby forming a porous bio-implant according to one embodiment of the present invention.

The porous bio-implant has an inner solid tissue and an outer porous layer. The inner solid tissue increases a durability of the bio-implant. The outer porous layer b allows for bone growth or fibrous tissue growth and malleable to allow it to conform to various shapes, thereby providing a strong, solid support when fixed to the bone and increasing a life span of the bio-implant. A pore size of the porous layer b is preferably in a range between 100 μm and 200 μm.

In greater detail, the metal powder 111, 111a or 111b in the pyrex tube 112, 112a or 112b is sintered by an electro discharge sintering (EDS) technique to forming pores on an outer surface of the porous bio-implant and form a solid core on an inner portion of the porous bio-implant. This mechanism is performed by combining a pinch pressure required to transform and squeeze the metal powder 111, 111a or 111b and a heat energy required to weld the metal powder 111, 111a or 111b.

A relationship between the heat energy and the solid core size is analyzed using experimental data as follows: a size of the solid core is 2.24 μm when a heat energy is 977 [J], and a size of the solid core is 2.47 μm when a heat energy is 1,340 [J]. It is understood that a size of the solid core is proportion to a heat energy.

A surface roughness of the porous bio-implant depends on a size of the metal powder 111, 111a or 111b. The solid core, a processing size, a processing rate, and a durability can be controlled by varying a capacity of the condenser 90, that is, varying an amount of an electric energy charged in the condenser 90.

Figure 11:
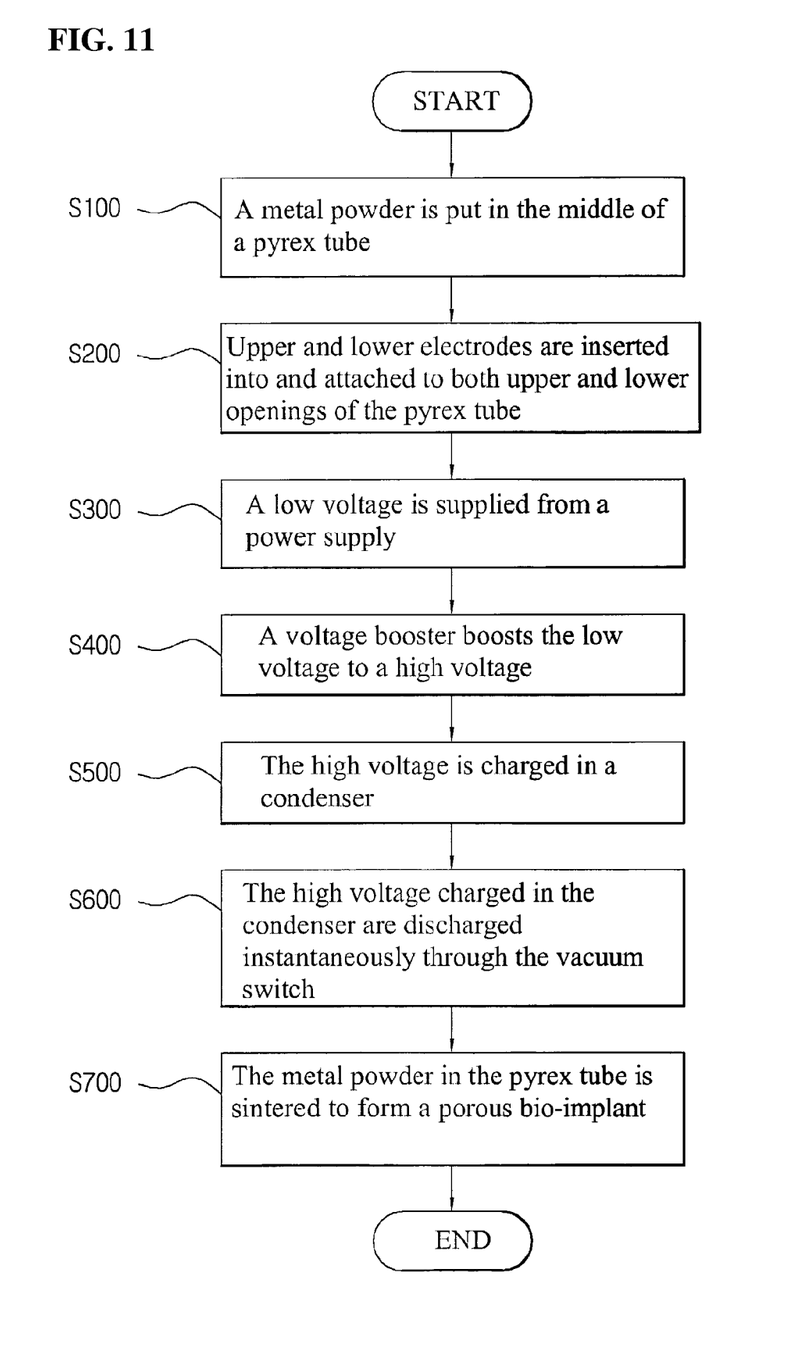
FIG. 11 is a flow chart illustrating a process of manufacturing a porous bio-implant according to one embodiment of the present invention.

FIG. 11 is a flow chart illustrating a process of manufacturing a porous bio-implant according to one embodiment of the present invention.

First, the metal powder 111, 111a or 111b is put in the middle of the pyrex tube 112, 112a or 112b (step S100). The upper and lower electrodes 113, 113a or 113b are inserted into and attached to both upper and lower openings of the pyrex tube 112, 112a or 112b (step S200).

A low voltage of 100 volts or 200 volts is supplied from the power supply 60 (step S300). The voltage booster 70 boosts the low voltage to a high voltage of 1000 volts to 5000 volts and preferably to a high voltage of 2500 volts (step S400). The high voltage passes through the first switch 80 and charges the condenser 90 (step S500).

The high voltage charged in the condenser 90 are discharged instantaneously through the vacuum switch 100 (step S600) to sinter the metal powder 111, 111a or 111b in the pyrex tube 112, 112a or 112b, thereby forming a porous bio-implant (step S700).

Figure 12:
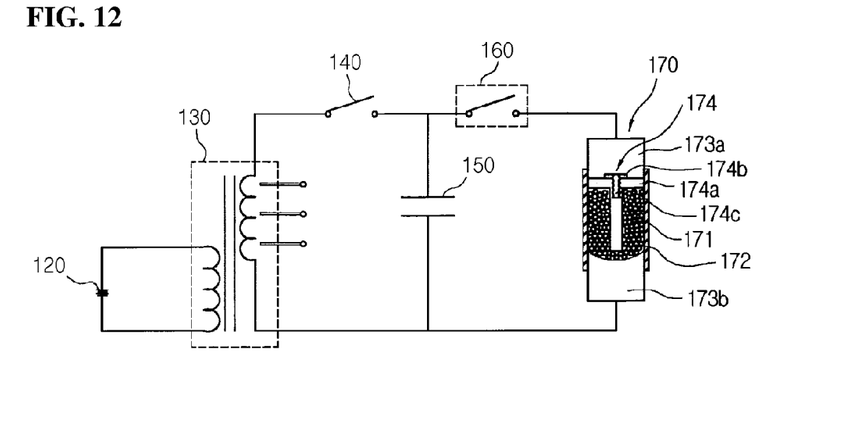
FIG. 12 is a circuit diagram illustrating a porous bio-implant manufacturing system according to another embodiment of the present invention.
Figure 13:
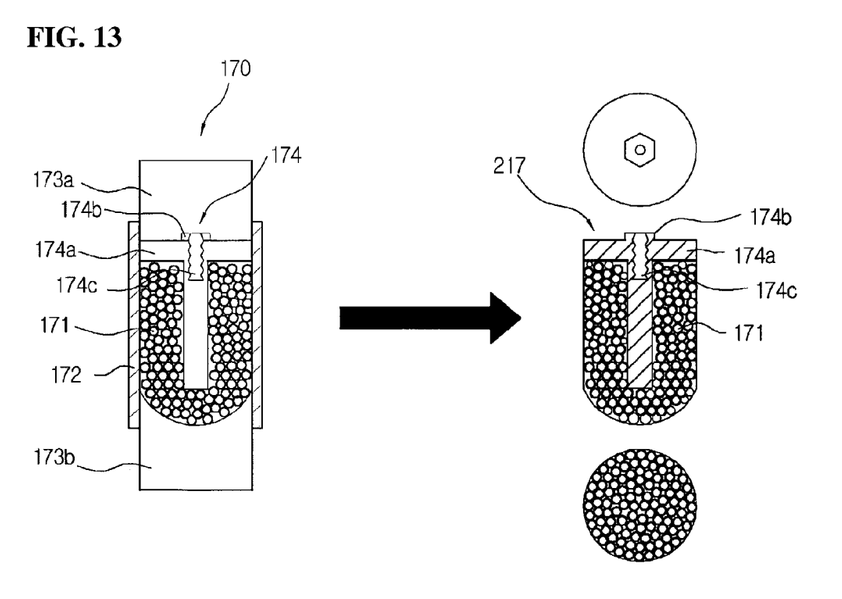
FIG. 13 is a cross-sectional view illustrating a porous bio-implant manufactured according to another embodiment of the present invention.

FIG. 12 is a circuit diagram illustrating a porous bio-implant manufacturing system according to another embodiment of the present invention. FIG. 13 is a cross-sectional view illustrating a porous bio-implant manufactured according to another embodiment of the present invention.

The porous bio-implant manufacturing system according to another embodiment of the present invention includes a power supply 120, a voltage booster 130, a first switch 140, a condenser 150, a vacuum switch 160, and a porous bio-implant manufacturing apparatus 170.

A low voltage of 100 volts or 200 volts is supplied from the power supply 120. The voltage booster 130 boosts the low voltage to a high voltage of 1000 volts to 5000 volts and preferably to a high voltage of 2500 volts. The high voltage passes through the first switch 140 and charges the condenser 150. The high voltage charged in the condenser 150 are discharged instantaneously through the vacuum switch 160.

The porous bio-implant manufacturing unit 170 includes a pyrex tube 172, upper and lower electrodes 173a and 173b, and a connecting member 174.

The pyrex tube 172 is hollow and is preferably made of quartz. The pyrex tube 172 can have various shapes. The upper and lower electrodes 173a and 173b are made of copper or brass.

The connecting member 174 includes a connecting member main 174a, a header portion 174b and a screw hole 174c. The connecting member main 174a preferably has a cross-section of a cross shape. The header portion 174b is formed on an upper central portion of the connecting member main 174a and preferably has a hexagon. The screw hole 174c is formed to a predetermined depth under the header portion 174b. Preferably, a distance between opposite sides of the header portion 174b is 2.7 mm, and a diameter of the screw hole 174c is 2.0 mm. The connecting member 174 can have various shapes.

The connecting member 174 is inserted into the pyrex tube 172 through an upper opening of the pyrex tube 172. A metal powder 171 is inserted into the middle of the pyrex tube 172 through a lower opening of the pyrex tube 172.

The upper electrode 173a is inserted through the upper opening of the pyrex tube 172 and rested on the upper surface of the connecting member 174. The lower electrode 173b having a concave surface is inserted through the lower opening of the pyrex tube 172. The upper and lower electrodes 173a and 173b are preferably made of Cu, brass, Gr, Ag—W, Cu—W, or Pt. The upper surface of the lower electrode 173b can have various shapes other than a concave shape.

Operation of the porous bio-implant manufacturing system is described below.

A low voltage of 100 volts or 200 volts is supplied from the power supply 130. The voltage booster 140 boosts the low voltage to a high voltage of 1000 volts to 5000 volts and preferably to a high voltage of 2500 volts. The high voltage passes through the first switch 140 and charges the condenser 150.

The high voltage charged in the condenser 150 are discharged instantaneously through the vacuum switch 160 to sinter the metal powder 171 in the pyrex tube 172, thereby forming a porous bio-implant integrally with the connecting member 174.

The porous bio-implant has an inner solid tissue and an outer porous layer. The inner solid tissue increases a durability of the bio-implant. The outer porous layer allows for bone growth or fibrous tissue growth and malleable to allow it to conform to various shapes, thereby providing a strong, solid support when fixed to the bone and increasing a life span of the bio-implant. A pore size of the porous layer is preferably in a range between 100 μm and 200 μm. A surface roughness of the porous bio-implant depends on a size of the metal powder 171. A compression strength of the porous bio-implant is determined by a size of the connecting member 174.

The porous bio-implant having the connecting member 174 formed integrally therewith is manufactured by combining a pinch pressure required to transform and squeeze the metal powder 171 and a heat energy required to weld the metal powder 171.

Figure 14:
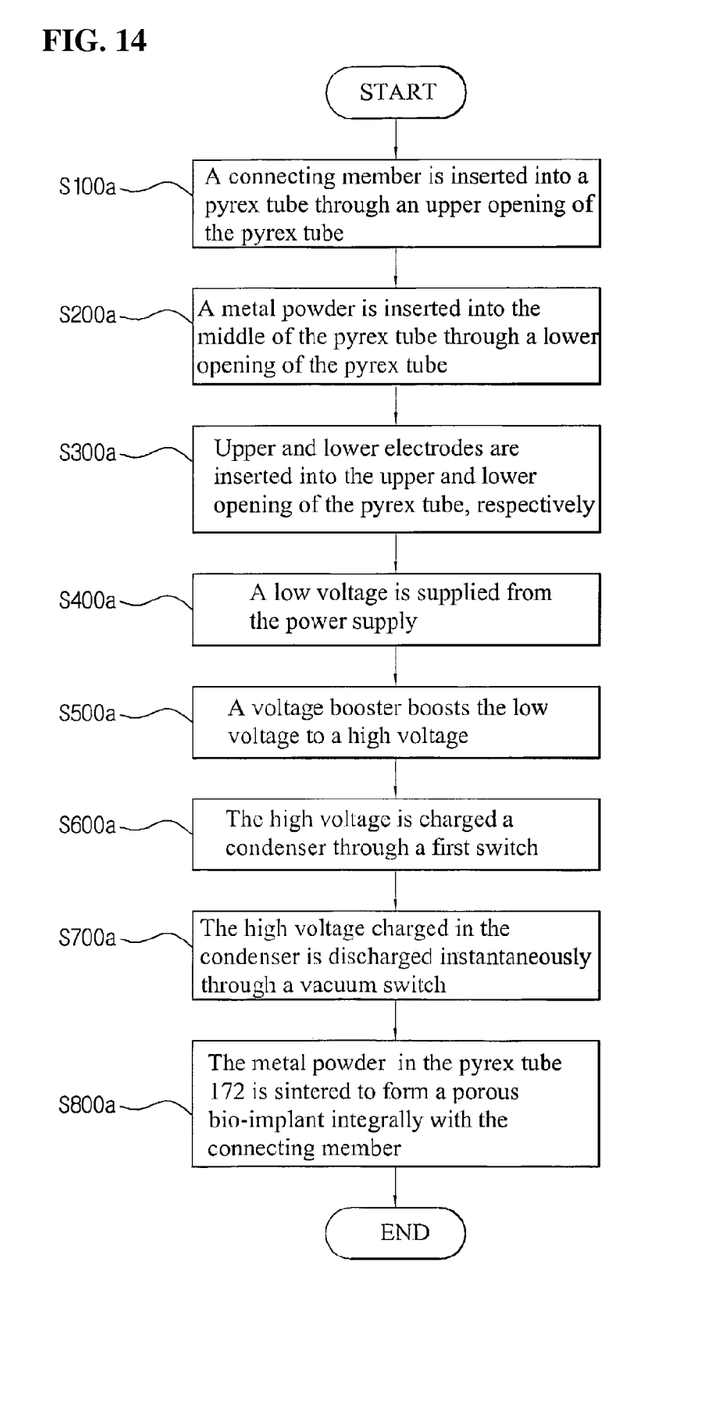
FIG. 14 is a flow chart illustrating a process of manufacturing a porous bio-implant according to another embodiment of the present invention.

FIG. 14 is a flow chart illustrating a process of manufacturing the porous bio-implant according to another embodiment of the present invention.

The connecting member 174 is inserted into the pyrex tube 172 through the upper opening of the pyrex tube 172 (step S100a). A metal powder 171 is inserted into the middle of the pyrex tube 172 through the lower opening of the pyrex tube 172 (step S200a).

The upper electrode 173a is inserted through the upper opening of the pyrex tube 172 and rested on the upper surface of the connecting member 174. The lower electrode 173b having a concave surface is inserted through the lower opening of the pyrex tube 172 (step S300a).

A low voltage of 100 volts or 200 volts is supplied from the power supply 120 (step S400a). The voltage booster 130 boosts the low voltage to a high voltage of 1000 volts to 5000 volts and preferably to a high voltage of 2500 volts (step S500a). The high voltage is charged the condenser 150 through the first switch 140 (step S600a).

The high voltage charged in the condenser 150 is discharged instantaneously through the vacuum switch 160 (step S700a) to sinter the metal powder 171 in the pyrex tube 172, thereby forming a porous bio-implant integrally with the connecting member 174 (step S800a).

INDUSTRIAL APPLICABILITY

As described herein before, the porous bio-implant has the following advantages. Since the porous bio-implant is integrally formed with the connecting member, a subsequent manufacturing process is not required, leading a simplified manufacturing process, a high throughput, and a high processing precision. A compression strength of the porous bio-implant can be adjusted by adjusting a size of the connecting member.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A method of manufacturing a porous-bio-implant having a connecting member formed integrally therewith, comprising the steps of:
    inserting a connecting member into an upper opening of a pyrex tube;
    inserting a metal powder into the pyrex tube through a lower opening of the pyrex tube;
    inserting an upper electrode through the upper opening of the pyrex tube and resting the upper electrode on an upper surface of the connecting member, and inserting a lower electrode through the lower opening of the pyrex tube;
    supplying a low voltage from a power supply that is connected to the upper and lower electrodes;
    boosting the low voltage to a high voltage by subjecting the low voltage to a voltage booster;
    charging the high voltage boosted by the voltage booster in a condenser through a first switch; and
    discharging the high voltage charged in the condenser instantaneously through a vacuum switch to sinter the metal powder in the pyrex tube, thereby forming a bio-implant, having a porous outer layer and a inner solid tissue, integrally with the connecting member.

2. The method of claim 1, wherein inserting a connecting member further comprises inserting a connecting member, which includes a connecting member main, a header portion integrally formed on an upper central portion of the connecting member main and a screw aperture, into an upper opening of a pyrex tube.

3. The method of claim 1, wherein supplying a low voltage further comprises supplying a voltage in the range of about 100 volts to about 200 volts from a power supply that is connected to the upper and lower electrodes.

4. The method of claim 1, wherein boosting the low voltage to a high voltage further comprises boosting the low voltage to a high voltage in the range of about 1000 volts to about 5000 volts.

5. The method of claim 1, wherein boosting the low voltage to a high voltage further comprises boosting the low voltage to a high voltage of about 2500 volts.

6. The method of claim 1, further comprising pressurizing the metal powder in the pyrex tube by applying pinch pressure between the upper and lower electrodes.

7. The method of claim 1, further comprising choosing the metal powder based on a size to determine a surface roughness of the resulting porous bio-implant.

8. The method of claim 1, further comprising choosing the connecting member based on a size to determine a compression strength of the resulting bio-implant.

* * * * *